United States Patent
Andree et al.

(10) Patent No.: US 6,262,291 B1
(45) Date of Patent: Jul. 17, 2001

(54) SUBSTITUTED N-(CYANOPHENYL) AMINOALKENAMIDES THEREFOR AND PROCESS FOR THEIR PREPARATION

(75) Inventors: Roland Andree; Mark Wilhelm Drewes, both of Langenfeld; Reinhard Lantzsch, Wuppertal; Heinz-Jürgen Wroblowsky, Langenfeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/661,690

(22) Filed: Sep. 14, 2000

Related U.S. Application Data

(62) Division of application No. 09/117,518, filed on Jul. 30, 1998, which is a continuation of application No. PCT/EP97/00353, filed on Jan. 27, 1997, now Pat. No. 6,169,182.

(30) Foreign Application Priority Data

Feb. 8, 1996 (DE) ................................ 196 04 582

(51) Int. Cl.$^7$ ................................ C07C 255/50
(52) U.S. Cl. ............................................ 558/414
(58) Field of Search ................................ 558/414

(56) References Cited

U.S. PATENT DOCUMENTS

| 4,169,106 | * | 9/1979 | Diamond et al. | ................. | 260/558 |
| 5,593,945 | | 1/1997 | Andree et al. | ................. | 504/243 |
| 5,759,957 | | 6/1998 | Andree et al. | ................. | 504/243 |

* cited by examiner

Primary Examiner—Robert W. Ramsuer
Assistant Examiner—Ebenezer Sackey
(74) Attorney, Agent, or Firm—Norris McLaughlin & Marcus

(57) ABSTRACT

The invention relates to a novel process for preparing substituted cyanophenyluracils of the general formula (I)

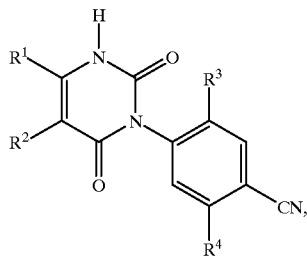

(I)

in which $R^1$, $R^2$, $R^3$ and $R^4$ are each as defined in the description, said compounds being known as herbicidally active compounds, to novel substituted N-(cyanophenyl) aminoalkenamides as intermediates therefor and to an inventive process for their preparation.

4 Claims, No Drawings

SUBSTITUTED N-(CYANOPHENYL) AMINOALKENAMIDES THEREFOR AND PROCESS FOR THEIR PREPARATION

This application is a division of U.S. Ser. No. 09/117,518, filed on Jul. 30, 1998, and now allowed U.S. Pat. No. 6,169,182, which is, in turn, a 371 of PCT/EP97/00353, filed on Jan. 27, 1997.

The invention relates to a novel process for preparing substituted cyanophenyluracils, said compounds being known as herbicidally active compounds, to novel substituted N-(cyanophenyl)aminoalkenamides as intermediates therefor and to an inventive process for their preparation.

It is known that certain substituted cyanophenyluracils can be prepared by reaction of appropriate aminoalkenoic esters with appropriate cyanophenyl isocyanates or with cyanophenylurethanes in the presence of reaction auxiliaries, such as, for example, sodium hydride (cf. EP 648749). However, with this procedure, yield and quality of the resulting products are not always entirely satisfactory, and the reaction components required are not very suitable for industrial purposes.

Furthermore, it is known that certain substituted phenyluracils can be prepared by reaction of appropriate substituted N-(phenyl)aminoalkenamides with suitable carbonic acid derivatives (cf. WO 95/32952). However, the synthetic croup described in this publication includes many steps and is complicated.

The present invention, accordingly, provides (a) a process for preparing substituted cyanophenyluracils of the general formula (1)

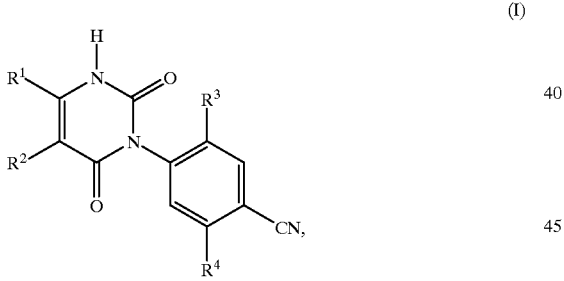

in which
$R^1$ represents optionally substituted alkyl,
$R^2$ represents hydrogen, halogen or alkyl,
$R^3$ represents hydrogen or halogen and
$R^4$ represents amino, halogen or the grouping —N($R^5$)SO$_2$R$^6$,
 in which
  $R^5$ represents hydrogen or represents respectively optionally substituted alkyl, alkylcarbonyl, alkylsulphonyl, cycloalkylcarbonyl, cycloalkylsulphonyl, arylcarbonyl or arylsulphonyl and
  $R^6$ represents respectively optionally substituted alkyl, cycloalkyl or aryl, characterized in that substituted N-(cyanophenyl)aminoalkenamides of the general formula (II)

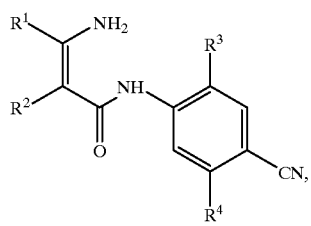

in which
$R^1$, $R^2$, $R^3$ and $R^4$ are each as defined above,
are reacted with carbonic acid derivatives of the general formula (III)

in which
$Z^1$ and $Z^2$ are identical or different and each represents halogen, alkoxy, aryloxy, imidazolyl or triazolyl,
if appropriate in the presence of a reaction auxiliary and if appropriate in the presence of a diluent at temperatures between –20° C. and +150° C., (b) novel substituted N-(cyanophenyl)aminoalkenamides of the general formula (II)

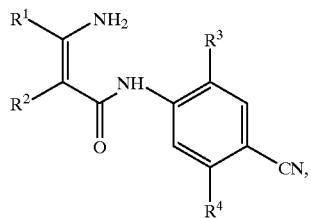

in which,
$R^1$ represents optionally substituted alkyl,
$R^2$ represents hydrogen, halogen or alkyl,
$R^3$ represents hydrogen or halogen and
$R^4$ represents amino, halogen or the grouping —N($R^5$)SO$_2$R$^6$,
 in which
  $R^5$ represents hydrogen or represents respectively optionally substituted alkyl, alkylcarbonyl, alkylsulphonyl, cycloalkylcarbonyl, cycloalkylsulphonyl, arylcarbonyl or arylsulphonyl and
  R6 represents respectively optionally substituted alkyl, cycloalkyl or aryl, and (c) a process for preparing substituted N-(cyanophenyl)aminoalkenamides of the general formula (II), characterized in that cyanophenylpyrimidinones of the general formula (IV)

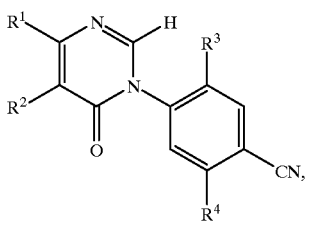

(IV)

in which
R$^1$, R$^2$, R$^3$ and R$^4$ are each as defined above
are reacted with basic compounds in the presence of a diluent at temperatures between −20° C. and +100° C.

The present invention also provides a novel preparative route to substituted cyanophenyluracils of the general formula (I), which combines the steps described above in a general manner under (c) and (a).

It is surprising that this novel route gives substituted cyanophenyluracils of the general formula (I) in a much more simple way and also in higher yields and improved quality. Especially the smooth ring-opening reaction of cyanophenylpyrimidinones of the formula (IV) to give substituted N-(cyanophenyl)aminoalkenamides of the formula (II) constitutes a very surprising new way of preparing substituted N-(aryl)-β-aminoalkenamides.

The invention preferably relates to the preparation of compounds of the formula (I) and also of novel compounds of the formula (II), in which in each case R$^1$ represents optionally fluorine- and/or chlorine-substituted alkyl having 1 to 4 carbon atoms, R$^2$ represents hydrogen, fluorine, chlorine, bromine or alkyl having 1 to 4 carbon atoms, R$^3$ represents hydrogen, fluorine, chlorine or bromine and R$^4$ represents amino, fluorine, chlorine or the grouping —N(R$^5$)SO$_2$R$^6$ in which R$^5$ represents hydrogen or represents respectively optionally fluorine- and/or chlorine-substituted alkyl, alkylcarbonyl or alkylsulphonyl having in each case 1 to 6 carbon atoms in the alkyl groups, represents respectively optionally fluorine- and/or chlorine-substituted cycloalkylcarbonyl or cycloalkylsulphonyl having in each case 3 to 6 carbon atoms in the cycloalkyl groups, or represents respectively optionally fluorine- and/or chlorine-substituted phenylcarbonyl or phenylsulphonyl, and R$^6$ represents optionally fluorine- and/or chlorine-substituted alkyl having 1 to 6 carbon atoms, represents optionally fluorine- and/or chlorine-substituted cycloalkyl having 3 to 6 carbon atoms, or represents respectively optionally fluorine- and/or chlorine-substituted phenyl.

The invention relates in particular to the preparation of compounds of the formula (I) and to novel compounds of the formula (II) in which in each case R$^1$ represents respectively optionally fluorine- and/or chlorine-substituted methyl or ethyl, R$^2$ represents hydrogen, fluorine, chlorine, bromine, methyl or ethyl, R$^3$ represents hydrogen, fluorine or chlorine and R$^4$ represents fluorine, chlorine or the grouping —N(R$^5$)SO$_2$R$^6$ in which, R$^5$ represents hydrogen or represents respectively optionally fluorine- and/or chlorine-substituted methyl, ethyl, n- or i-propyl, acetyl, propionyl, methylsulphonyl or ethylsulphonyl, represents respectively optionally fluorine- and/or chlorine-substituted cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, or represents respectively optionally fluorine- and/or chlorine-substituted phenylcarbonyl or phenylsulphonyl, and R$^6$ represents respectively optionally fluorine- and/or chlorine-substituted methyl, ethyl, n- or i-propyl, n-, i-, s- or t-butyl, represents respectively optionally fluorine- and/or chlorine-substituted cyclopropyl, cyclobutyl, cyclopentyl or cyclohexyl, or represents respectively optionally fluorine- and/or chlorine-substituted phenyl.

If, for example, in the process step described above under (c) (process (c)) 3-(4-cyano-2,5-difluorophenyl)-6-trifluoromethylpyrimidin-4-one is used as starting material, and the resulting product is reacted according to the process step described above under (a) (process (a)) with, for example, phosgene, then the reaction may be outlined by the following scheme:

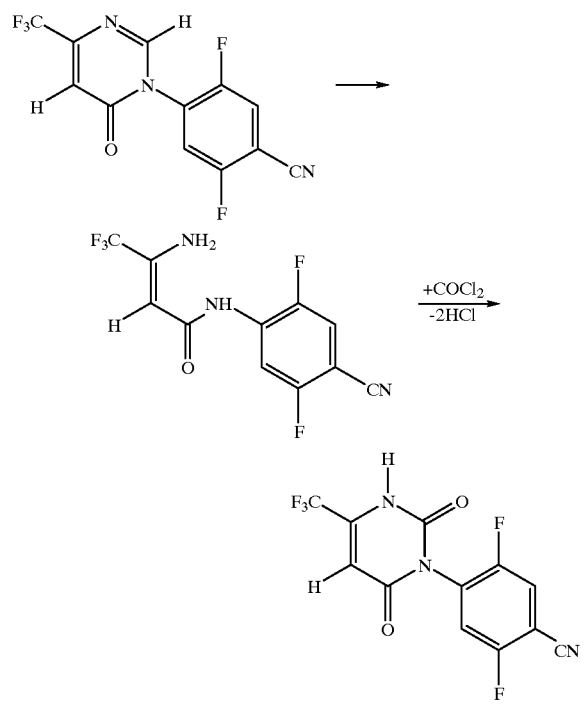

The carbonic acid derivatives to be used as starting materials in the process (a) according to the invention for preparing compounds of the formula (I) are defined in a general way by formula (III). In Formula (III), Z$^1$ and Z$^2$ are identical or different and preferably represent fluorine, chlorine, bromine, C$_1$–C$_4$-alkoxy, phenoxy, imidazolyl or triazolyl, in particular chlorine, methoxy, ethoxy or phenoxy.

Examples of starting materials of the formula (III) are:

Phosgene (and also its "dimers" or "trimers" —diphosgene or triphosgene), dimethyl carbonate, diethyl carbonate, diphenyl carbonate, methyl chloroformate, ethyl chloroformate and also carbonyl-bis-imidazole.

The starting materials of the formula (III) are known chemicals for synthesis.

The cyanophenylpyrimidinones to be used as starting materials in process (c) according to the invention for preparing compounds of the formula (II) are defined in a general way by the formula (IV). In the formula (IV), $R^1$, $R^2$, $R^3$ and $R^4$ preferably or in particular have those meanings which have already been mentioned above, in connection with the description of the compounds of the formula (I) according to the invention, as being preferred or particularly preferred for $R^1$, $R^2$, $R^3$ and $R^4$.

The starting materials of the formula (IV) are known and/or can be prepared by known processes (cf. DE 4431218, Preparation Examples).

The process (c) according to the invention is carried out using a basic compound. Suitable basic compounds include all customary inorganic or organic bases. These include, for example, alkaline earth metal or alkali metal hydrides, hydroxides, amides, alkoxides, acetates, carbonates or bicarbonates, such as, for example, lithium hydride, sodium hydride potassium hydride or calcium hydride, sodium amide or potassium amide, sodium methoxide or potassium methoxide, sodium ethoxide or potassium ethoxide, sodium n- or i-propoxide or potassium n- or i-propoxide, sodium t-butoxide or potassium t-butoxide, lithium hydroxide, sodium hydroxide, potassium hydroxide, magnesium hydroxide or calcium hydroxide, ammonium hydroxide, sodium acetate or potassium acetate, ammonium acetate, sodium carbonate, potassium carbonate, magnesium carbonate or calcium carbonate, sodium bicarbonate or potassium bicarbonate, ammonium carbonate and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

Alkali metal carbonates, such as, for example, sodium carbonate or potassium carbonate, alkali metal hydroxides, such as, for example, sodium hydroxide or potassium hydroxide, and alkali metal alkoxides, such as, for example, sodium methoxide or potassium methoxide, sodium ethoxide or potassium ethoxide, sodium t-butoxide or potassium t-butoxide, are particularly preferred for use as basic compounds in the process (c) according to the invention.

Suitable diluents for carrying out the process (c) according to the invention are water and organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxan, tetrahydrofuran and ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, sulphoxides, such as dimethylsulphoxide, alcohols, such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether, mixtures thereof with water or pure water.

Water or alcohols, such as, for example, methanol or ethanol, are particularly preferred for use as diluents in the process (c) according to the invention.

When carrying out the process (c) according to the invention, the reaction temperatures may be varied within a relatively wide range. In general, the reaction is carried out at temperatures between −20° C. and +100° C., preferably between −5° C. and +80° C., in particular between +10° C. and +60° C.

The process (c) according to the invention is usually carried out under atmospheric pressure. However, it is also possible to carry out the process (c) according to the invention under elevated or reduced pressure—in general between 0.1 bar and 10 bar.

In the practice of the process (c) according to the invention, generally 0.9 to 1.5 mol, preferably 0.95 to 1.2 mol of a basic compound are employed per mole of cyanophenylpyrimidinone of the formula (IV).

In general, the reactants are mixed at room temperature—or if necessary with slight cooling—and the reaction mixture is stirred at the particular temperature required until the reaction has ended.

Work-up and isolation of products may be performed in the usual manner. For example, the mixture is shaken with water and with a virtually water-immiscible organic solvent, such as, for example, methylene chloride, the organic phase is separated off and dried. The solvent is distilled off under reduced pressure and the residue is, if necessary, purified according to a customary method (for example chromatography, recrystallization). However, the crude product of process (c) may, if appropriate, be used without further purification for reaction according to process (a).

The process (a) according to the invention for preparing compounds of the formula (I) is preferably carried out in the presence of a suitable reaction auxiliary. Suitable reaction auxiliaries are, in general, the customary inorganic or organic bases or acid acceptors. These include, preferably, alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n- or i-, s- or t-butoxide or potassium n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethyl-aniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methylpiperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Preferred diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofurane or ethylene glycol dimethyl ether or ethylene glycol diethyl ether, ketones, such as acetone, butanone or methyl isobutyl ketone; nitriles, such as acetonitrile, propionitrile, or benzonitrile, amides, such as N,N-dimethyl-formamide, N,N-dimethyl-acetamide, N-methyl-formamide, N-methyl-pyrrolidone or hexamethylphosphoric triamide; esters such as methyl acetate or ethyl acetate, and sulphoxides, such as dimethyl sulphoxide.

When carrying out the process (a) according to the invention, the reaction temperatures may be varied over a relatively wide range. In general, the reaction is carried out at temperatures between −20° C. and +150° C., preferably between −10° C. and +120° C., in particular between 0°C. and 100° C.

The process (a) according to the invention is generally carried out under atmospheric pressure. However, it is also possible to carry out process (a) according to the invention under elevated or reduced pressure—in general between 0.1 bar and 10 bar.

In the practice of process (a) according to the invention, generally 1.0 to 5.0 mol, preferably 1.1 to 2.5 mol of carbonic acid derivative of the formula (III) and, if appropriate, 1.0 to 5.0 mol, preferably 1.2 to 2.5 mol of reaction auxiliary are employed per mole of substituted N-(cyanophenyl)aminocrotonamide of the formula (II). The reaction is carried out, and the reaction products are worked up and isolated, according to known methods.

The cyanophenyluracils to be prepared according to the invention are already known as herbicidally active compounds (cf. EP 648749).

PREPARATION EXAMPLES

Example 1

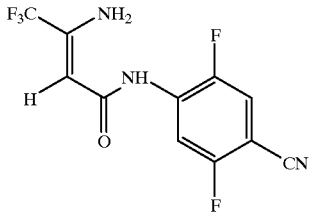

(Process (c))

30.3 g (0.10 mol) of 3-(4-cyano-2,5-difluoro-phenyl)-6-trifluoromethyl-pyrimid-4-one, 20 ml of 5N aqueous sodium hydroxide solution (0.10 mol of NaOH) and 300 ml of water are mixed at room temperature (about 20° C.), and the mixture is stirred at this temperature for about 20 hours. The crystalline reaction product is isolated by filtration with suction, washed with water, and dried in a desiccator over phosphorus(V) oxide.

27.7 g (93.3% pure, i.e. 89% of theory) of N-(4-cyano-2,5-difluoro-phenyl)-3-amino-4,4,4-trifluoro-2-butenamide of melting point 127° C. are obtained.

Example 2

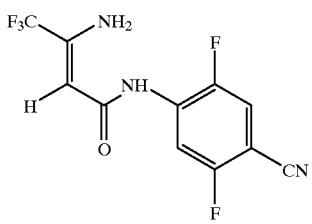

(Process (c))

0.8 g (2.7 mmol) of 3-(4-cyano-2,5-difluoro-phenyl)-6-trifluoromethyl-pyrimid-4-one, 0.15 g (2.7 mmol) of sodium methoxide and 10 ml of ethanol are mixed at room temperature (about 20° C.), and the mixture is stirred at this temperature for about one hour. The mixture is then concentrated using water pump vacuum, the residue is shaken with water/methylene chloride, and the organic phase is separated off, dried with sodium sulphate, and filtered. The solvent is carefully removed from the filtrate using water pump vacuum.

0.6 g (76% of theory) of N-(4-cyano-2,5-difluoro-phenyl)-3-amino-4,4,4-trifluoro-2-butenamide of melting point 127° C. are obtained.

Example 3

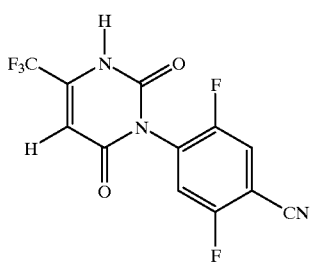

(Process (a))

1.56 g (5 mmol) of N-(4-cyano-2,5-difluoro-phenyl)-3-amino-4,4,4-trifluoro-2-butenamide (93.3% pure) are dissolved in 20 ml of tetrahydrofurane, and 0.3 g of an 80% strength suspension of sodium hydride in paraffin oil are added. The mixture is stirred for about 30 minutes at about 20° C. 1.28 g (5.6 mmol) of diphenyl carbonate are subsequently added, and the reaction mixture is heated under reflux for about 15 hours. After cooling, the mixture is concentrated using water pump vacuum, the residue is taken up in water, and the pH is adjusted to 3 by addition of 2N hydrochloric acid. The resulting crystalline product is isolated by filtration with suction and dried under reduced pressure over phosphorus(V) oxide.

1.65 g (79.7% pure, i.e. 83% of theory) of 1-(4-cyano-2,5-difluoro-phenyl)-3,6-dihydro-2.,6-dioxo-4-trifluoromethyl-1(2H)-pyrimidine of melting point 208° C. are obtained.

Example 4

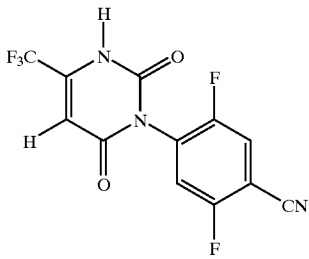

(Process (a))

9.4 g (30 mmol) of N-(4-cyano-2,5-difluoro-phenyl)-3-amino-4,4,4-trifluoro-2-5 butenamide (93.3% pure) are dissolved in 200 ml of toluene, and 6 ml of pyridine and 0.3 g of 4-dimethylamino-pyridine are added. At an internal temperature of about 40° C., about 5 g of phosgene are introduced and the reaction mixture is subsequently stirred for about a further 4 hours at about 40° C. After cooling, 200 ml of water are added and, after shaking thoroughly, the resulting crystalline product is isolated by filtration with suction and dried on clay.

3.7 g (39% of theory) of 1-(4-cyano-2,5-difluoro-phenyl)-3,6-dihydro-2,6-dioxo-4-trifluoromethyl-1(2H)-pyrimidine of melting point 208° C. are obtained.

Starting Material of the Formula (IV)

Example (IV-1)

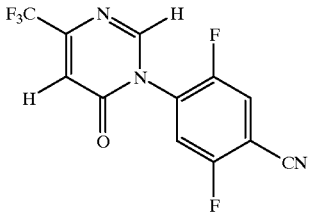

A mixture of 3.0 g (18.3 mmol) of 6-trifluoromethyl-pyrimidine-4-one, 2.5 g (18.3 mmol) of potassium carbonate and 50 ml of dimethyl sulphoxide is stirred at 20° C. for 15 hours. 2.9 g (18.3 mmol) of 2,4,5-trifluoro-benzonitrile are then added, and the mixture is stirred at 60° C. for 8 hours. After concentration of the mixture, the residue is stirred with water and the resulting crystalline product is isolated by filtration with suction.

2.7 g (49% of theory) of 3-(4-cyano-2,5-difluoro-phenyl)-6-trifluoromethylpyrimidine-4-one of melting point 95° C. are obtained.

What is claimed is:
1. Substituted N-(cyanophenyl)aminoalkenamides of the formula (II)

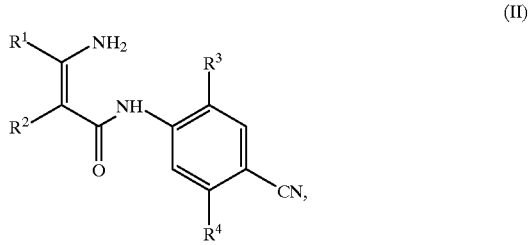

characterized in that
$R^1$ represents optionally substituted alkyl,
$R^2$ represents hydrogen, halogen or alkyl,
$R^3$ represents hydrogen or halogen and
represents amino, halogen or the grouping —N($R^5$)SO$_2R^6$,
in which
$R^5$ represents hydrogen or represents respectively optionally substituted alkyl, alkylcarbonyl, alkylsulphonyl, cycloalkylcarbonyl, cycloalkylsulphonyl, arylcarbonyl or arylsulphonyl and
$R^6$ represents respectively optionally substituted alkyl, cycloalkyl or aryl.
2. Substituted N-(cyanophenyl)aminoalkenamides of the general formula (II) according to claim 1, characterized in that
represents optionally fluorine- and/or chlorine-substituted alkyl having 1 to 4 carbon atoms,
$R^2$ represents hydrogen, fluorine, chlorine, bromine or alkyl having 1 to 4 carbon atoms,
$R^3$ represents hydrogen, fluorine, chlorine or bromine and
$R^4$ represents amino, fluorine, chlorine or the grouping —N($R^5$)SO$_2R^6$ in which
$R^5$ represents hydrogen or represents respectively optionally fluorine- and/or chlorine-substituted alkyl, alkylcarbonyl or alkylsulphonyl having in each case 1 to 6 carbon atoms in the alkyl groups, represents respectively optionally fluorine- and/or chlorine-substituted cycloalkylcarbonyl or cycloalkylsulphonyl having in each case 3 to 6 carbon atoms in the cycloalkyl groups, or represents respectively optionally fluorine- and/or chlorine-substituted phenylcarbonyl or phenylsulphonyl, and
$R^6$ represents optionally fluorine- and/or chlorine-substituted alkyl having 1 to 6 carbon atoms, represents optionally fluorine- and/or chlorine-substituted cycloalkyl having 3 to 6 carbon atoms, or represents respectively optionally fluorine- and/or chlorine-substituted phenyl.
3. Substituted N-(cyan phenyl)aminoalkenamides of the general formula (II) according to claim 1, characterized in that
$R^1$ represents respectively optionally fluorine- and/or chlorine-substituted methyl or ethyl,
$R^2$ represents hydrogen, fluorine, chlorine, bromine, methyl or ethyl,
$R^3$ represents hydrogen, fluorine or chlorine and
$R^4$ represents fluorine, chlorine or the grouping —N($R^5$)SO$_2 R^6$ in which,
$R^5$ represents hydrogen or represents respectively optionally fluorine- and/or chlorine-substituted methyl, ethyl, n- or 1-propyl, acetyl, propionyl, methylsulphonyl or ethylsulphonyl, represents respectively optionally fluorine- and/or chlorine-substituted cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, or represents respectively optionally fluorine- and/or chlorine-substituted phenylcarbonyl or phenylsulphonyl, and $R^6$ represents respectively optionally fluorine- and/or chlorine-substituted methyl, ethyl, n- or i-propyl, n-, i-, s- or t-butyl, represents respectively optionally fluorine- and/or chlorine-substituted cyclopropyl, cyclobutyl, cyclopentyl or cyclohexyl, or represents respectively optionally fluorine- and/or chlorine-substituted phenyl.

4. Process for preparing substituted N-(cyanophenyl) aminoalkenamides of the general formula (II)

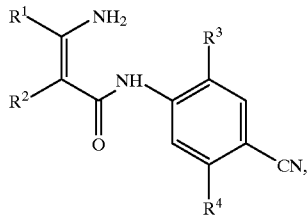

(II)

in which $R^1$, $R^2$, $R^3$ and $R^4$ are each as defined in claim 1, characterized in that cyanophenylpyrimidinones of the general formula (IV)

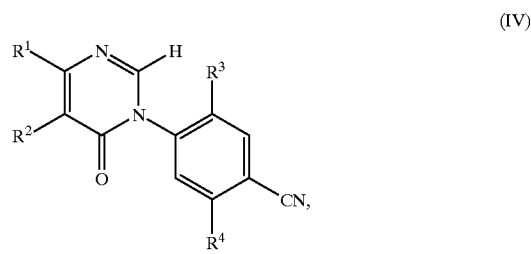

(IV)

in which $R^1$, $R^2$, $R^3$ and $R^4$ are each as defined in claim 1 are reacted with basic compounds in the presence of a diluent at temperatures between −20° C. and +100° C.

* * * * *

UNITED STATES PATENT AND TRADEMARK OFFICE
CERTIFICATE OF CORRECTION

PATENT NO.    : 6,262,291 B1
DATED         : July 17, 2001
INVENTOR(S)   : Roland Andree et al.

It is certified that error appears in the above-identified patent and that said Letters Patent is hereby corrected as shown below:

<u>Column 10,</u>
Line 20, before "represent" enter -- $R^4$ --

Signed and Sealed this

Eleventh Day of February, 2003

JAMES E. ROGAN
*Director of the United States Patent and Trademark Office*